United States Patent
Maubru et al.

(10) Patent No.: US 7,708,981 B2
(45) Date of Patent: May 4, 2010

(54) COSMETIC COMPOSITIONS COMPRISING AT LEAST ONE CROSSLINKED COPOLYMER, AT LEAST ONE INSOLUBLE MINERAL PARTICLE AND AT LEAST ONE POLYMER, AND USES THEREOF

(75) Inventors: Mireille Maubru, Chatou (FR); Serge Restle, Saint-Prix (FR); Béatrice Perron, Jouy en Josas (FR)

(73) Assignee: L'Oreal S.A., Paris (FR)

( * ) Notice: Subject to any disclaimer, the term of this patent is extended or adjusted under 35 U.S.C. 154(b) by 1156 days.

(21) Appl. No.: 10/796,082

(22) Filed: Mar. 10, 2004

(65) Prior Publication Data

US 2004/0234485 A1 Nov. 25, 2004

Related U.S. Application Data

(60) Provisional application No. 60/454,620, filed on Mar. 17, 2003.

(30) Foreign Application Priority Data

Mar. 11, 2003 (FR) .................................. 03 02997

(51) Int. Cl.
| | |
|---|---|
| *A61Q 5/02* | (2006.01) |
| *A61Q 5/04* | (2006.01) |
| *A61Q 5/06* | (2006.01) |
| *A61Q 5/08* | (2006.01) |
| *A61Q 5/10* | (2006.01) |
| *A61Q 5/12* | (2006.01) |
| *A61Q 19/10* | (2006.01) |

(52) U.S. Cl. ..................... 424/70.11; 424/62; 424/70.2; 424/70.6; 424/401

(58) Field of Classification Search ........................ None
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,528,378 A | 10/1950 | Mannheimer | |
| 2,781,354 A | 2/1957 | Mannheimer | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,165,367 A | 8/1979 | Chakrabarti | |
| 4,166,894 A | 9/1979 | Schaper | |
| 4,172,887 A | 10/1979 | Vanlergerghe et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |

(Continued)

FOREIGN PATENT DOCUMENTS

| | | |
|---|---|---|
| EP | 0 122 324 A1 | 10/1984 |
| EP | 0 186 507 A2 | 7/1986 |
| EP | 0 342 834 A2 | 11/1989 |
| EP | 0 412 704 A2 | 2/1991 |
| EP | 0 412 707 A1 | 2/1991 |
| EP | 0 582 152 A2 | 2/1994 |
| GB | 1 546 809 | 5/1979 |
| GB | 2 315 215 | 1/1998 |
| WO | WO 93/23009 | 11/1993 |
| WO | WO 93/23446 | 11/1993 |
| WO | WO 95/00578 | 1/1995 |
| WO | WO 98/18431 | 5/1998 |
| WO | WO 01/74311 | 10/2001 |
| WO | WO 01/76552 | 10/2001 |

OTHER PUBLICATIONS

WO /2002/096377 , Abstract, May 2002.*

(Continued)

*Primary Examiner*—Jyothsna A Venkat
(74) *Attorney, Agent, or Firm*—Finnegan, Henderson, Farabow, Garrett & Dunner, L.L.P.

(57) ABSTRACT

Disclosed herein are a cosmetic composition comprising, in a cosmetically acceptable medium, at least one crosslinked copolymer comprising at least one methacrylic acid unit and at least one $C_1$-$C_4$ alkyl acrylate unit, at least one polymer chosen from cationic and amphoteric polymers and at least one water-insoluble solid mineral particle chosen from clays, particles comprising alumina, particles comprising at least 10% by weight of calcium carbonate, and selenium sulphide, and the use of the composition for washing and/or conditioning keratin materials, such as hair or skin.

15 Claims, No Drawings

U.S. PATENT DOCUMENTS

| | | | |
|---|---|---|---|
| 4,381,919 A | 5/1983 | Jacquet et al. | |
| 4,422,853 A | 12/1983 | Jacquet et al. | |
| 4,445,521 A | 5/1984 | Grollier et al. | |
| 4,579,732 A | 4/1986 | Grollier et al. | |
| 4,591,610 A | 5/1986 | Grollier | |
| 4,608,250 A | 8/1986 | Jacquet et al. | |
| 4,693,935 A | 9/1987 | Mazurek | |
| 4,719,099 A | 1/1988 | Grollier et al. | |
| 4,728,571 A | 3/1988 | Clemens et al. | |
| 4,761,273 A | 8/1988 | Grollier et al. | |
| 4,777,040 A | 10/1988 | Grollier et al. | |
| 4,803,221 A | 2/1989 | Bair | |
| 4,839,166 A | 6/1989 | Grollier et al. | |
| 4,948,579 A | 8/1990 | Jacquet et al. | |
| 4,957,732 A | 9/1990 | Grollier et al. | |
| 4,970,066 A | 11/1990 | Grollier et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,089,252 A | 2/1992 | Grollier et al. | |
| 5,139,037 A | 8/1992 | Grollier et al. | |
| 5,196,189 A | 3/1993 | Jacquet et al. | |
| 5,334,376 A | 8/1994 | Robbins et al. | |
| 5,580,494 A * | 12/1996 | Sandhu et al. | 510/125 |
| 5,958,392 A | 9/1999 | Grollier et al. | |
| 6,635,702 B1 * | 10/2003 | Schmucker-Castner et al. | 524/291 |
| 7,258,852 B2 * | 8/2007 | Maubru | 424/70.11 |
| 2003/0103927 A1 * | 6/2003 | Maubru | 424/70.12 |
| 2003/0103929 A1 * | 6/2003 | Maubru | 424/70.16 |
| 2003/0108503 A1 * | 6/2003 | Maubru et al. | 424/70.12 |
| 2003/0118538 A1 | 6/2003 | Krause et al. | |
| 2004/0001796 A9 * | 1/2004 | Maubru | 424/70.12 |
| 2004/0197355 A1 * | 10/2004 | Perron et al. | 424/401 |
| 2004/0197356 A1 * | 10/2004 | Perron et al. | 424/401 |
| 2005/0158267 A1 | 7/2005 | Krause et al. | |

OTHER PUBLICATIONS

WO /2002/096385 , Abstract, May 2002.*
"New Gels and Thickeners for Cosmetics: Structure—Application—Formulation," SÖFW Journal, vol. 128, No. 5, 2002, pp. 16-18, and 20.
English language Derwent Abstract of EP 1 210 932, Jun. 5, 2002.
French Search Report for FR 631602 (Priority Application for U.S. Appl. No. 10/796,082), Nov. 19, 2003.
ANOM. "New gels and thickners for cosmetics: structure, application, formulation," SOFW Journal (2002) 128(5): 16-18, 20, XP009021303.
English language Derwent abstract of DE 199 46 784 A1.
English language abstract of EP 0 080 976 A1.
English language Derwent abstract of EP 1 210 932 A2.
English language Derwent abstract of FR 2 589 476 A1.

* cited by examiner

COSMETIC COMPOSITIONS COMPRISING AT LEAST ONE CROSSLINKED COPOLYMER, AT LEAST ONE INSOLUBLE MINERAL PARTICLE AND AT LEAST ONE POLYMER, AND USES THEREOF

This application claims benefit of U.S. Provisional Application No. 60/454,620, filed Mar. 17, 2003.

Disclosed herein are novel cosmetic compositions comprising, in a cosmetically acceptable medium, at least one crosslinked copolymer comprising at least one methacrylic acid unit and at least one $C_1$-$C_4$ alkyl acrylate unit, at least one polymer chosen from cationic and amphoteric polymers and at least one water-insoluble solid mineral particle chosen from clays, particles comprising alumina, particles comprising calcium carbonate, and selenium sulphide.

It is well known that hair that has been sensitized (i.e. damaged and/or embrittled) to varying degrees due to the action of atmospheric agents or mechanical or chemical treatments, such as dyeing, bleaching and/or permanent-waving, can often be difficult to disentangle and to style, and can lack softness.

It has already been recommended to use conditioners, such as cationic polymers, amphoteric polymers, or silicones, in compositions for washing or caring for keratin materials, such as hair, in order to facilitate the disentangling of the hair and to give it softness and suppleness. However, the cosmetic advantages mentioned above can unfortunately also be accompanied, on dried hair, by certain undesirable cosmetic effects, for example, lankness of the hairstyle (lack of lightness of the hair) and a lack of smoothness (hair not uniform from the root to the end).

Additionally, the use of cationic or amphoteric polymers for this purpose may have various drawbacks. On account of their high affinity for hair, some of these polymers become deposited on the hair, in a substantial amount, during repeated use and can lead to undesirable effects, such as an unpleasant, laden feel, stiffening of the hair, and adhesion between the fibers of the hair, which affects the styling of the hair. These drawbacks can be accentuated in the case of fine hair, which lacks liveliness and volume.

It has already been proposed to use particles in rinse-out compositions, so as to improve the feel and appearance of the hair. For example, U.S. Pat. No. 5,334,376 proposes the addition of calcium carbonate particles to hair-conditioning compositions comprising a silicone, a fatty alcohol and an amide.

Additionally, it has been proposed, in Patent Application No. DE 199 46 784, to use particles of different oxides, hydroxides, carbonates, silicates or phosphates in hair compositions, to reduce the greasy appearance of the hair. It is generally envisaged to combine these particles with standard shampoo ingredients.

However, it has been found that these particles may lead to the formation of an unattractive layer at the surface of the shampoo, which can be detrimental to the performance qualities of the shampoo. To avoid the appearance of this phenomenon, stabilizers, such as crosslinked acrylic polymers of the Carbopol type are frequently used. However, these stabilizers can have the drawback of reducing the cosmetic performance qualities of shampoos, for example, by making the hair coarser and more laden.

In summary, it has been found that the current cosmetic compositions comprising cationic or amphoteric polymers are not entirely satisfactory.

Cosmetic compositions, such as detergent compositions, comprising at least one crosslinked copolymer comprising at least one methacrylic acid unit and at least one $C_1$-$C_4$ alkyl acrylate unit as a stabilizer or suspension agent for water-insoluble ingredients, for instance, silicones or fatty substances, are known in the prior art. Such compositions have been described, for example, in Patent Application No. WO 01/76552. The foam qualities and the cosmetic properties obtained with these compositions are not sufficiently satisfactory in all applications.

In one embodiment, the present inventors have now discovered that the combination of at least one crosslinked copolymer comprising at least one methacrylic acid unit and at least one $C_1$-$C_4$ alkyl acrylate unit, of at least one polymer chosen from cationic and amphoteric polymers, and of particular mineral particles makes it possible to overcome at least one of these drawbacks.

Specifically, in one embodiment, it has been found that the use of the at least one crosslinked copolymer in the compositions disclosed herein may make it possible to obtain on keratin materials, such as on hair, good cosmetic properties, for example, with regard to the lightness, the softness, the smooth feel, the suppleness and the manageability of dried hair. In a further embodiment, it has also been found that the compositions disclosed herein, may make it possible to give the hair texture (increased sensation of thickness) and better hold of the hairstyle.

The compositions disclosed herein can be stable and can have an attractive visual appearance. The working properties (appearance, consistency, abundance of lather, removal of the lather) may also be very satisfactory.

In another embodiment, the compositions disclosed herein can improve the softness of the skin when applied to it, such as in the form of a bubble bath or a shower gel.

Thus, disclosed herein are novel cosmetic compositions comprising, in a cosmetically acceptable medium, at least one crosslinked copolymer comprising at least one methacrylic acid unit and at least one $C_1$-$C_4$ alkyl acrylate unit, at least one polymer chosen from cationic and amphoteric polymers and at least one water-insoluble solid mineral particle chosen from clays, particles comprising alumina, particles comprising at least 10% by weight of calcium carbonate, and selenium sulphide.

Further disclosed herein is the use of the composition as defined above to give hair at least one of texture, lightness, softness, a smooth feel, and suppleness.

Also disclosed herein, is a process for treating keratin materials, such as hair, comprising applying to the keratin materials the cosmetic compositions disclosed herein.

As used herein, the term "keratin materials" means hair, eyelashes, eyebrows, skin, nails, mucous membranes and scalp. For example, the keratin material is hair.

As used herein, the term "unit" means the polymerized form of the monomer. For example a methacrylic acid unit is the polymerized form of methacrylic acid.

Also disclosed herein is the use of at least one crosslinked copolymer comprising at least one methacrylic acid unit and at least one $C_1$-$C_4$ alkyl acrylate unit in, or for the manufacture of, a cosmetic composition comprising at least one polymer chosen from cationic and amphoteric polymers and at least one water-insoluble solid mineral particle chosen from clays, particles comprising alumina, particles comprising at least 10% by weight of calcium carbonate, and selenium sulphide.

As used herein, the term "water-insoluble" compounds refers to compounds that are insoluble in water to a concentration of greater than or equal to 0.1% by weight in water at 25° C., i.e., they do not form a macroscopic isotropic and transparent solution.

One of the characteristics of the disclosure is the presence of at least one crosslinked copolymer comprising at least one methacrylic acid unit and at least one $C_1$-$C_4$ alkyl acrylate unit. The crosslinked copolymer comprising at least one methacrylic acid unit and at least one $C_1$-$C_4$ alkyl acrylate unit means a crossklinked copolymer comprising of at least one methacrylic acid unit and at least one alkyl acrylate unit, wherein the alkyl acrylate is chosen from $C_1$-$C_4$ alkyl acrylates.

In the crosslinked copolymer disclosed herein, the at least one methacrylic acid unit can be present in an amount ranging from 20% to 80% by weight, for example, from 25% to 70% by weight, and further, for example, from 35% to 60% by weight, relative to the total weight of the copolymer.

In the crosslinked copolymer disclosed herein, the at least one alkyl acrylate unit can be present in an amount ranging from 15% to 80% by weight, for example, from 25% to 75% by weight, and further, for example, from 40% to 65% by weight, relative to the total weight of the copolymer. The alkyl acrylate can, for example, be chosen from methyl acrylate, ethyl acrylate and butyl acrylate. In one embodiment, the alkyl acrylate is ethyl acrylate.

The copolymer disclosed herein is partially or totally crosslinked with at least one crosslinking agent. The at least one crosslinking agent can be chosen, for example, from polyunsaturated compounds, such as polyethylenically unsaturated compounds. These compounds can be chosen, for example, from polyalkenyl ethers of sucrose, polyalkenyl ethers of polyols, diallyl phthalates, divinylbenzene, allyl (meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, castor oil derivatives and polyol derivatives manufactured from unsaturated carboxylic acids.

The at least one crosslinking agent that may also be used include, for example, unsaturated monomers comprising at least one reactive group capable of reacting with an unsaturation to form a crosslinked copolymer.

The content of the at least one crosslinking agent generally ranges from 0.01% to 5% by weight, for example, from 0.03% to 3% by weight, and further, for example, from 0.05% to 1% by weight, relative to the total weight of the copolymer.

According to one embodiment, the at least one crosslinked copolymer disclosed herein may, for example, be in the form of a dispersion in water. The number-average size of the copolymer particles in the dispersion generally ranges from 10 nm to 500 nm, for example, from 20 nm to 200 nm, and further, for example, from 50 nm to 150 nm.

These copolymers are described, for example, in Patent Application No. WO 01/76552.

For example, the crosslinked methacrylic acid/ethyl acrylate copolymer in the form of an aqueous dispersion of 30% active material manufactured and sold under the name Carbopol Aqua SF-1 by the company Noveon may be used.

The concentration of the at least one crosslinked copolymer generally ranges from 0.01% to 10% by weight, and, for example, from 0.1% to 5% by weight, relative to the total weight of the composition.

The particles disclosed herein may be in any form, for example, in the form of spheres, flakes, needles, platelets or totally random forms.

As used herein, the term "primary particle size" means the maximum size that it is possible to measure between two diametrically opposite points on an individual particle. The size may be determined by transmission electron microscopy or by measuring the specific surface area via the BET method.

The clays may be of natural or synthetic origin. In one embodiment, the clays are of natural origin.

The compositions, in accordance with the disclosure, may comprise at least one clay.

Clays are products that are well known, and are described, for example, in the book "Minéralogie des argiles [Mineralogy of clays], S. Caillère, S. Hénin, M. Rautureau, 2nd edition 1982, Masson."

Non-limiting examples of clays that may be mentioned include clays of the kaolinite family, such as kaolinite, dickite and nacrite, clays of the halloysite, dombassite, antigorite, benthierine and pyrophyllite family, montmorillonites, beidellite, vermiculites, talc, stevensite, hectorites, saponites, chlorites and sepiolite.

The clays may also be chemically modified with various compounds, such as acrylic acids, polysaccharides, for example, carboxymethylcellulose and organic cations.

According to one embodiment of the present disclosure, the clay can be chosen from kaolinite, montmorillonites and hectorites.

The selenium sulphide used herein may comprise one selenium atom per two sulphur atoms. It may also have a $Se_xSy$ cyclic structure wherein $x+y=8$.

The selenium disulphide that may be used herein is a powder, the particles of which have a number-average size of less than 200 microns and, for example, less than 25 microns.

The particles comprising alumina disclosed herein, for example, comprise at least 70% by weight of alumina and, for example, more than 90% by weight of alumina. The particles may have a number-average primary size ranging from 2 to 200 nm and, for example, from 5 to 50 nm.

The alumina particles disclosed herein may comprise optionally hydrated alumina, for instance, boehmite.

The particles comprising at least 10% by weight of calcium carbonate, as disclosed herein, comprise, for example, at least 70% by weight of calcium carbonate and further, for example, more than 90% by weight of calcium carbonate. The particles may have a number-average primary size ranging from 2 nm to 2 microns, for example, from 5 to 500 nm, and further, for example, from 10 to 250 nm.

As disclosed herein, the particles may, for example, be chosen from solid particles formed entirely of calcium carbonate. Calcium carbonate may constitute all or part of the core of the particle, wherein the core can be coated with another constituent, for instance, oxides, silicates and metals. Calcium carbonate may also exclusively form the coating of a substrate of a different chemical constituent, such as oxides, silicates and metals.

In one embodiment, where the particles comprise calcium carbonate and other fillers, the calcium carbonate is in free form and does not form chemical bonds with the other fillers. Then this is a case, for example, of an alloy between the calcium carbonate and other fillers, such as with metal oxides and metalloids, obtained, for example, by thermal fusion of these various constituents.

When the particles comprising at least 10% by weight of calcium carbonate also comprise at least one metal oxide or metalloid oxide, this oxide can be chosen, for example, from silicone oxide, boron oxide and aluminium oxide.

For example, the particles can comprise at least 50% by weight of calcium carbonate and, for instance at least 70% by weight of calcium carbonate, and further, for example, the particles can comprise more than 90% by weight of calcium carbonate.

In one embodiment, the particles comprising at least 10% by weight of calcium carbonate are particles of substantially pure calcium carbonate.

The calcium carbonate used herein may be of natural origin or may be of synthetic origin. If the calcium carbonate is of synthetic origin, it may be obtained from calcium oxide, calcium peroxide, calcium acetate or calcium ethoxide.

The insoluble solid mineral particles can be present in an amount ranging, for example, from 0.001% to 20% by weight, and further, for example, from 0.005% to 15% by weight, and even further, for example, from 0.01% to 10% by weight, relative to the total weight of the composition.

The cationic polymers that may be used herein may be chosen from all those already known per se as improving the cosmetic properties of the hair, for example, those described in Patent Application No. EP-A-0 337 354 and in French Aatent Application Nos. 2,270,846, 2,383,660, 2,598,611, 2,470,596 and 2,519,863.

As used herein, the term "cationic polymer" means any polymer comprising at least one group chosen from cationic groups and groups that may be ionized into cationic groups.

For example, the cationic polymers can be chosen from polymers comprising units comprising at least one amine group chosen from primary, secondary, tertiary and quaternary amine groups, wherein the at least one amine group is part of a main polymer chain or a side substituent attached directly to the main polymer chain.

The cationic polymers used may, for example, have a number-average molecular mass ranging from 500 to $5 \times 10^6$ and, for example, from $10^3$ to $3 \times 10^6$.

Among the cationic polymers that may be used, non-limiting mention may, for example, be made of polymers of the polyamine, polyamino amide and polyquaternary ammonium type. These products are known in the art.

The polymers of the polyamine, polyamino amide and polyquaternary ammonium type that may be used herein, and that may, for example, be mentioned, are those described in French Patents Nos. 2,505,348 and 2,542,997. Among these polymers, non-limiting mention may be made of:

(1) homopolymers and copolymers derived from acrylic and methacrylic esters and amides and comprising at least one of the units of the following formulae:

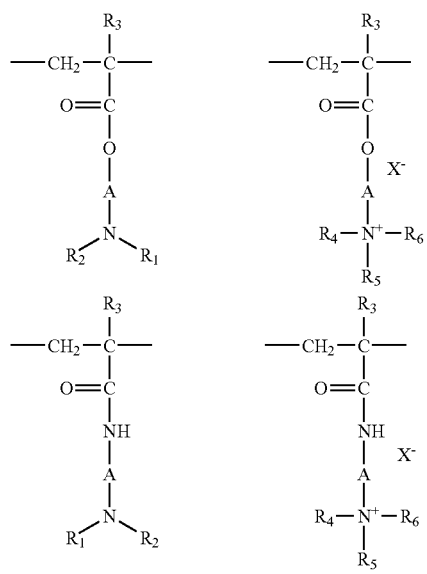

wherein:

$R_3$, which may be identical or different, can be chosen from hydrogen and a $CH_3$ group;

A, which may be identical or different, is chosen from linear and branched alkyl groups comprising from 1 to 6 carbon atoms, for example, 2 or 3 carbon atoms, and hydroxyalkyl groups comprising from 1 to 4 carbon atoms;

$R_4$, $R_5$, $R_6$, which may be identical or different, are each chosen from alkyl groups comprising from 1 to 18 carbon atoms, such as from 1 to 6 carbon atoms, and a benzyl group;

$R_1$, and $R_2$, which may be identical or different, can each be chosen from hydrogen and alkyl groups comprising from 1 to 6 carbon atoms, such as methyl and ethyl;

$X^-$ is an anion chosen from anions derived from an acid chosen from mineral and organic acids, such as a methyl sulphate anion and halides, such as chloride and bromide.

The copolymers of family (1) can further comprise at least one unit derived from comonomers which may be chosen from the family of acrylamides, methacrylamides, diacetone acrylamides, acrylamides and methacrylamides substituted on the nitrogen with at least one group chosen from lower ($C_1$-$C_4$) alkyls, acrylic and methacrylic acids and esters thereof, vinyllactams, such as vinylpyrrolidone and vinylcaprolactam, and vinyl esters.

Thus, among the copolymers of family (1), non-limiting mention may be made of:

copolymers of acrylamide and of dimethylaminoethyl methacrylate quaternized with dimethyl sulphate or with a dimethyl halide, such as the product sold under the name Hercofloc by the company Hercules, copolymers of acrylamide and of methacryloyloxyethyltrimethylammonium chloride described, for example, in Patent Application No. EP-A-080 976 and sold under the name Bina Quat P 100 by the company Ciba Geigy, copolymers of acrylamide and of methacryloyloxyethyltrimethylammonium methosulphate sold under the name Reten by the company Hercules, optionally quaternized vinylpyrrolidone/dialkylaminoalkyl acrylate or methacrylate copolymers, such as the products sold under the name "Gafquat" by the company ISP, such as, for example, "Gafquat® 734" or "Gafquat® 755", or the products known as "Copolymer 845, 958 and 937". These polymers are described in detail in French Patent Nos. 2,077, 143 and 2,393,573, dimethylaminoethyl methacrylate/vinylcaprolactam/vinylpyrrolidone terpolymers, such as the product sold under the name Gaffix® VC 713 by the company ISP, vinylpyrrolidone/methacrylamidopropyldimethylamine copolymers sold, for example, under the name Styleze® CC 10 by ISP, and quaternized vinylpyrrolidone/dimethylaminopropylmethacrylamide copolymers, such as the product sold under the name "Gafquat® HS 100" by the company ISP.

(2) cationic polysaccharides, for example, cationic celluloses and cationic galactomannan gums. Among the cationic polysaccharides, non-limiting mention may be made, for example, of cellulose ethers comprising quaternary ammonium groups, cationic cellulose copolymers and cellulose derivatives grafted with a water-soluble quaternary ammonium monomer and cationic galactomannan gums.

The cellulose ether derivatives comprising quaternary ammonium groups, which are described in French Patent No. 1,492,597, such as the polymers sold under the names "JR" (JR 400, JR 125, JR 30M) or "LR" (LR 400, LR 30M) by the company Amerchol. These polymers are also defined in the CTFA dictionary as hydroxyethylcellulose quaternary ammoniums that have reacted with an epoxide substituted with a trimethylammonium group.

The cationic cellulose copolymers or cellulose derivatives grafted with a water-soluble quaternary ammonium monomer are described, for example, in U.S. Pat. No. 4,131,576. For example, non-limiting mention may be made of hydroxyalkylcelluloses, for instance, hydroxymethyl-, hydroxyethyl- and hydroxypropylcelluloses grafted, for example, with at least one salt chosen from methacryloylethyltrimethylammonium, methacrylamidopropyltrimethylammonium and dimethyldiallylammonium salts.

The commercial products corresponding to this definition are, for example, the products sold under the names "Celquat® L 200" and "Celquat® H 100" by the company National Starch.

The cationic galactomannan gums are described, for example, in U.S. Pat. Nos. 3,589,578 and 4,031,307, such as guar gums comprising trialkylammonium cationic groups. Use may be made, for example, of guar gums modified with a salt (e.g. chloride) of 2,3-epoxypropyltrimethylammonium.

Such products are sold, for instance, under the trade names Jaguar® C13 S, Jaguar® C 15, Jaguar® C 17 or Jaguar® C162 by the company Rhodia.

(3) polymers comprising piperazinyl units and divalent alkylene or hydroxyalkylene groups comprising at least one chain chosen from straight and branched chains, optionally interrupted by at least one entity chosen from oxygen, sulphur and nitrogen atoms and aromatic and heterocyclic rings, as well as the oxidation and/or quaternization products of these polymers. Such polymers are described, for example, in French Patent Nos. 2,162,025 and 2,280,361;

(4) water-soluble polyamino amides prepared, for example, by polycondensation of at least one acidic compound with at least one polyamine; and polyamino amides that are crosslinked with at least one entity chosen from epihalohydrins, diepoxides, dianhydrides, unsaturated dianhydrides, bis-unsaturated derivatives, bis-halohydrins, bis-azetidiniums, bis-haloacyidiamines, bis-alkyl halides or with an oligomer resulting from the reaction of a difunctional compound which is reactive with at least one entity chosen from bis-halohydrins, abis-azetidiniums, bis-haloacyidiamines, bis-alkyl halides, epihalohydrins, diepoxides and bis-unsaturated derivatives; wherein the crosslinking agent being used is present in an amount ranging from 0.025 to 0.35 mol per amine group of the polyamino amide; and wherein the polyamino amides are optionally alkylated and if the polyamino amides comprise at least one tertiary amine functional group, the at least one tertiary amine functional group is optionally quaternized. Such polymers are described, for example, in French Patent Nos. 2,252,840 and 2,368,508;

(5) polyaminoamide derivatives resulting from the condensation of polyalkylene polyamines with polycarboxylic acids followed by alkylation with difunctional agents. Non-limiting mention may be made, for example, of adipic acid/dialkylamino-hydroxyalkyldialkylenetriamine polymers wherein the alkyl group comprises from 1 to 4 carbon atoms and, for example, is chosen from methyl, ethyl and propyl. Such polymers are described, for example, in French Patent No. 1,583, 363.

Among these derivatives, mention may be made, for example, of the adipic acid/dimethylaminohydroxypropyl/diethylenetriamine polymers sold under the name "Cartaretine® F, F4 or F8" by the company Sandoz.

(6) polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms. The molar ratio between the polyalkylene polyamine and the dicarboxylic acid ranges from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Polymers of this type are sold, for example, under the name "Hercosett® 57" by the company Hercules Inc. or under the names "PD 170" or "Delsette® 101" by the company Hercules in the case of the adipic acid/epoxypropyl/diethylenetriamine copolymer.

(7) cyclopolymers of alkyldiallylamine or of dialkyldiallylammonium, such as the homopolymers or copolymers comprising, as main constituent of the chain, units corresponding to formula (II) or (III):

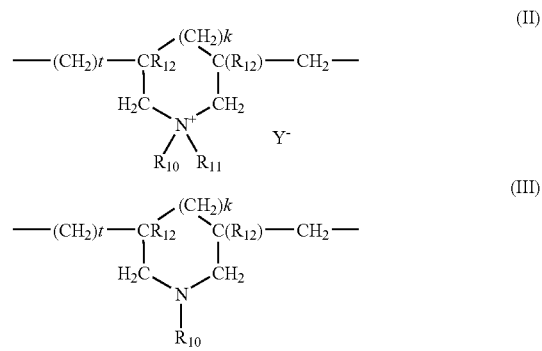

wherein k and t, which may be identical or different, are each equal to 0 or 1, the sum k+t is equal to 1; $R_{12}$, which may be identical or different, is chosen from hydrogen and a methyl group; $R_{10}$ and $R_{11}$, which may be identical or different, can each be chosen from alkyl groups comprising from 1 to 6 carbon atoms, hydroxyalkyl groups wherein the alkyl group comprises, for example, from 1 to 5 carbon atoms, lower $C_1$-$C_4$ amidoalkyl groups, or $R_{10}$ and $R_{11}$ can form, together with the nitrogen atom to which they are attached, heterocyclic groups, such as piperidyl and morpholinyl; $Y^-$ is an anion, such as bromide, chloride, acetate, borate, citrate, tartrate, bisulphate, bisulphite, sulphate and phosphate. These polymers are described, for example, in French Patent No. 2,080, 759 and in its Certificate of Addition 2 190 406.

For example, $R_{10}$ and $R_{11}$, which may be identical or different, can each be chosen from alkyl groups comprising from 1 to 4 carbon atoms.

Among the polymers defined above, mention may be made, for example, of the dimethyldiallylammonium chloride homopolymer sold under the name "Merquat® 100" by the company Nalco (and its homologues of low weight-average molecular mass) and copolymers of diallyldimethylammonium chloride and of acrylamide, sold under the name "Merquat® 550".

(8) quaternary diammonium polymers comprising repeating units corresponding to the formula (IV):

'wherein:

R$_{13}$, R$_{14}$, R$_{15}$ and R$_{16}$, which may be identical or different, can each be chosen from aliphatic, alicyclic and arylaliphatic groups comprising from 1 to 20 carbon atoms and lower hydroxyalkylaliphatic groups, or R$_{13}$, R$_{14}$, R$_{15}$ and R$_{16}$, together or separately, can form, with the nitrogen atoms to which they are attached, heterocycles optionally comprising a second hetero atom other than nitrogen, or R$_{13}$, R$_{14}$, R$_{15}$ and R$_{16}$, which may be identical or different, are each chosen from linear and branched C$_1$-C$_6$ alkyl groups substituted with at least one substituent chosen from nitrile, ester, acyl and amide groups and groups of formulae: —CO—O—R$_{17}$-D and —CO—NH—R$_{17}$-D, wherein R$_{17}$ is chosen from alkylenes and D is chosen from quaternary ammonium groups;

A$_1$ and B$_1$, which may be identical or different, can each be chosen from polymethylene groups comprising from 2 to 20 carbon atoms, which may be linear or branched, saturated or unsaturated, and which optionally comprise, linked to or intercalated in the main chain, at least one entity chosen from aromatic rings, oxygen and sulphur atoms, and sulphoxide, sulphone, disulphide, amino, alkylamino, hydroxyl, quaternary ammonium, ureido, amide and ester groups, and X$_1^-$ is an anion derived from an acid chosen from inorganic and organic acids; or A$_1$, R$_{13}$ and R$_{15}$ can form, with the two nitrogen atoms to which they are attached, a piperazine ring; in addition, wherein if A$_1$ is chosen from linear and branched, saturated and unsaturated alkylene and hydroxyalkylene groups, B$_1$ is optionally chosen from groups of formula:

(CH$_2$)$_n$—CO-D-OC—(CH$_2$)$_n$—;

wherein D is chosen from:

a) glycol residues of formula: —O—Z—O—, wherein Z is chosen from linear and branched hydrocarbon-based groups and groups corresponding to one of the following formulae:

—(CH$_2$—CH$_2$—O)$_x$—CH$_2$—CH$_2$—

—[CH$_2$—CH(CH$_3$)—O]$_y$—CH$_2$—CH(CH$_3$)— wherein x and y, which may be identical or different, are each an integer ranging from 1 to 4, representing a defined and unique degree of polymerization or any number ranging from 1 to 4 representing an average degree of polymerization;

b) bis-secondary diamine residues, such as a piperazine derivative;

c) bis-primary diamine residues of formula: —NH—Y—NH—, wherein Y is chosen from linear and branched hydrocarbon-based groups, and divalent group of formula:

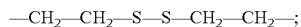
—CH$_2$—CH$_2$—S—S—CH$_2$—CH$_2$—;

d) ureylene groups of formula:

—NH—CO—NH—;

For example, X$^-$ is an anion, such as chloride or bromide. These polymers generally have a number-average molecular mass ranging from 1,000 to 100,000.

Polymers of this type are described, for example, in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

For example, it is possible to use polymers that comprise repeating units corresponding to the formula (V):

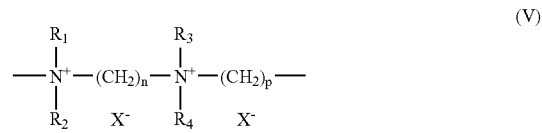

wherein R$_1$, R$_2$, R$_3$ and R$_4$, which may be identical or different, can each be chosen from alkyl and hydroxyalkyl groups comprising, for example, from 1 to 4 carbon atoms, n and p, which may be identical or different, are each an integer ranging from 2 to 20, and X$^-$ is an anion derived from an acid chosen from inorganic and organic acids.

One polymer comprising repeating units of formula (V) that can be used, for example, is one wherein R$_1$, R$_2$, R$_3$ and R$_4$ are each a methyl group and n=3, p=6 and X=Cl, which is known as Hexadimethrine chloride according to the INCI (CTFA) nomenclature.

(9) polyquaternary ammonium polymers comprising units of formula (VI):

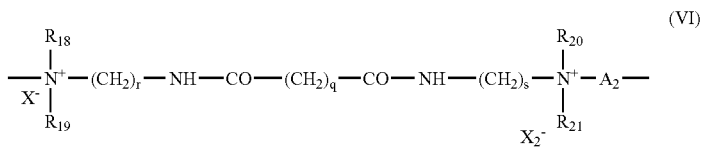

wherein:

R$_{18}$, R$_{19}$, R$_{20}$ and R$_{21}$, which may be identical or different, can each be chosen from hydrogen and methyl, ethyl, propyl, β-hydroxyethyl, β-hydroxypropyl and —CH$_2$CH$_2$(OCH$_2$CH$_2$)$_p$OH groups, wherein p is equal to 0 or to an integer ranging from 1 to 6, with the proviso that R$_{18}$, R$_{19}$, R$_{20}$ and R$_{21}$ do not simultaneously represent hydrogen, r and s, which may be identical or different, are each an integer ranging from 1 to 6, q is equal to 0 or to an integer ranging from 1 to 34, X$_2^-$ is an anion, such as a halide, A$_2$ is chosen from divalent groups and —CH$_2$—CH$_2$—O—CH$_2$—CH$_2$-group.

Such polymers are described, for example, in Patent Application No. EP-A-122 324.

Among these products, non-limiting mention may be made, for example, of the products "Mirapol® A 15", "Mirapol® AD1", "Mirapol® AZ1" and "Mirapol® 175" sold by the company Miranol.

(10) quaternary polymers of vinylpyrrolidone and of vinylimidazole, for instance, the products sold under the names Luviquat® FC 905, FC 550 and FC 370 by the company BASF.

(11) polyamines, for instance Polyquart® H sold by Cognis, referenced under the name Polyethylene Glycol (15) Tallow Polyamine in the CTFA dictionary.

(12) Optionally crosslinked methacryloyloxy($C_1$-$C_4$)alkyltri($C_1$-$C_4$)alkylammonium salt polymers, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, such as methylenebisacrylamide. For example, a crosslinked acrylamide/methacryloyloxyethyltrimethylammonium chloride copolymer (20/80 by weight) in the form of a dispersion comprising 50% by weight of the copolymer in mineral oil can be used. This dispersion is sold under the name "Salcare® SC 92" by the company Ciba. A crosslinked methacryloyloxyethyltrimethylammonium chloride homopolymer comprising about 50% by weight of the homopolymer in mineral oil or in a liquid ester can also be used. These dispersions are sold under the names "Salcare® SC 95" and "Salcare® SC 96" by the company Ciba.

Other cationic polymers that can be used herein include, for example, cationic proteins and cationic protein hydrolysates, polyalkyleneimines, such as polyethyleneimines, polymers comprising vinylpyridine or vinylpyridinium units, condensates of polyamines and of epichlorohydrin, quaternary polyureylenes and chitin derivatives.

For example, the polyalkyleneimines used herein can be chosen from polymers comprising from 6 to 20,000 repeating units. The polyalkyleneimines can, for example, be chosen from those comprising at least 5% of tertiary amine functional groups, for example, at least 10% of tertiary amine functional groups, and further, for example, at least 20% of tertiary amine functional groups. These polymers may be chosen from homopolymers and copolymers of linear, branched and dendrimeric structure.

These polymers can comprise the following repeating units:

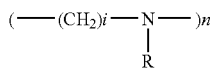

wherein:

i is an integer greater than or equal to 2 and, for example, less than or equal to 6, such as i=2;

n is an integer ranging from 6 to 20,000 and, for example, ranging from 8 to 2,500, R is chosen from hydrogen and units of formula

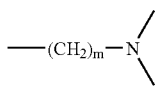

wherein m is an integer greater than or equal to 2, such as m=2.

For example, these polymers generally end in amine end functional groups, such as primary amines.

As disclosed herein, the polyalkyleneimines are, for example, chosen from poly($C_2$-$C_4$)alkyleneimines and such as polyethyleneimines.

The polyalkyleneimines disclosed herein generally have a weight-average molecular weight ranging from 300 to 100,000, for example, from 350 to 50,000 and further, for example, from 400 to 10,000.

The molecular weights are determined by quasi-elastic light scattering.

The polyalkyleneimines, for example, have a cationic charge density of less than or equal to 20 meq/g and, for instance, greater than or equal to 0.05 meq/g.

The charge density may be determined according to the Kjeldahl method, or calculated.

The polyalkyleneimines are described, for example, in the book "Polymer science Dictionary" 2nd edition, Mark Alger, Chapman & Hall, 1997.

The cationic polymers that may be used herein include, for example, quaternary cellulose ether derivatives, such as products sold under the name "JR 400" by the company Amerchol, cationic cyclopolymers, for example, dimethyidiallylammonium chloride homopolymers or copolymers sold under the names "Merquat 100" "Merquat 550" and "Merquat S" by the company Nalco, quaternary polymers of vinylpyrrolidone and of vinylimidazole, crosslinked homopolymers or copolymers of methacryloyloxy($C_1$-$C_4$)alkyltri($C_1$-$C_4$)alkylammonium salts, and polyalkyleneimines, such as polyethyleneimines, and mixtures thereof.

The amphoteric polymers that may be used herein may be chosen, for example, from polymers comprising units K and M randomly distributed in the polymer chain, wherein K is chosen from units derived from at least one monomer comprising at least one basic nitrogen and M is chosen from units derived from at least one acidic monomer comprising at least one group chosen from carboxylic and sulphonic groups, or K and M, which may be identical or different, may be chosen from groups derived from at least one monomer chosen from zwitterionic carboxybetaine and sulphobetaine monomers;

K and M, which may be identical or different, may also be chosen from cationic polymer chains comprising at least one amine group chosen from primary, secondary, tertiary and quaternary amine groups, wherein at least one of the amine groups comprises at least one group chosen from carboxylic and sulphonic groups linked via a hydrocarbon-based group, or K and M form part of a chain of a polymer comprising at least one α,β-dicarboxylic ethylene unit wherein one of the carboxylic groups has been made to react with a polyamine comprising at least one amine group chosen from primary and secondary amine groups.

For example, the amphoteric polymers corresponding to the above definition can be chosen from the following polymers:

(1) polymers resulting from the copolymerization of at least one monomer derived from at least one vinyl compound comprising at least one carboxylic group, such as acrylic acid, methacrylic acid, maleic acid, α-chloroacrylic acid, and at least one basic monomer derived from at least one substituted vinyl compound comprising at least one basic atom, such as dialkylaminoalkyl methacrylate and acrylate, dialkylaminoalkylmethacrylamide and -acrylamide. Such polymers are described in U.S. Pat. No. 3,836,537. Non-limiting mention may also be made of sodium acrylate/acrylamidopropyltrimethylammonium chloride copolymers sold under the name Polyquart KE 3033 by the company Cognis.

The vinyl compound may also be chosen from dialkyldiallylammonium salts, such as dimethyidiallylammonium chloride. The copolymers of acrylic acid and of the basic monomer are sold under the names Merquat 280, Merquat 295 and Merquat Plus 3330 by the company Nalco.

(2) Polymers comprising at least one unit derived from:

a) at least one monomer chosen from acrylamides and methacrylamides substituted on the nitrogen with at least one alkyl group, b) at least one acidic comonomer comprising at least one reactive carboxylic group, and c) at least one basic comonomer such as esters comprising at least one of primary, secondary, tertiary and quaternary amine substituents of acrylic and methacrylic acids and the product of quaternization of dimethylaminoethyl methacrylate with dimethyl or diethyl sulphate.

As disclosed herein, the N-substituted acrylamides or methacrylamides can be chosen, for example, from those wherein the alkyl groups comprise from 2 to 12 carbon atoms and, for example, N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen, for example, from acrylic acid, methacrylic acid, crotonic acid, itaconic acid, maleic acid and fumaric acid and alkyl monoesters, comprising from 1 to 4 carbon atoms, maleic and fumaric acids and anhydrides.

The basic comonomers can be chosen, for example, from aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer, such as the products sold under the name Amphomer or Lovocryl 47 by the company National Starch can, for example, be used.

(3) Crosslinked and partially or totally alkylated polyamino amides derived from polyamino amides of general formula:

$$-[CO-R_4-CO-Z]-\quad\quad\quad (VII)$$

wherein $R_4$ is chosen from divalent groups derived from at least one entity chosen from saturated dicarboxylic acids, monocarboxylic and dicarboxylic aliphatic acids comprising at least one ethylenic double bond, esters of lower alkanols, comprising from 1 to 6 carbon atoms, and of these acids, and groups derived from the addition of any one of the acids to a bis(primary) or bis(secondary) amine, and Z is chosen from bis(primary), mono- and bis(secondary) polyalkylenepolyamine groups and may, for example, be:

a) in proportions ranging from 60 to 100 mol %, the group of formula (VIII)

$$-NH-[(CH_2)_x-NH]_p-\quad\quad\quad (VIII)$$

wherein x=2 and p=2 or 3, or x=3 and p=2, and
this group is derived from diethylenetriamine, triethylenetetraamine or dipropylenetriamine;

b) in proportions ranging from 0 to 40 mol %, the radical (VIII) above, wherein x=2 and p=1 and the group is derived from ethylenediamine or the group derived from piperazine:

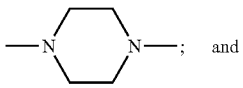

c) in proportions ranging from 0 to 20 mol %, the —NH—$(CH_2)_6$—NH— group derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of an entity chosen from acrylic acids, chloroacetic acids and alkane sultones, and salts thereof.

The saturated carboxylic acids may be chosen, for example, from acids comprising from 6 to 10 carbon atoms, such as adipic acid, 2,2,4-trimethyladipic acid and 2,4,4-trimethyladipic acid, terephthalic acid and acids comprising an ethylenic double bond, such as acrylic acid, methacrylic acid and itaconic acid.

The alkane sultones that may be used in alkylation are, for example, propane sultone and butane sultone, and the salts of the alkylating agents may, for example, be chosen from sodium and potassium salts.

(4) Polymers comprising zwitterionic units of formula (IX):

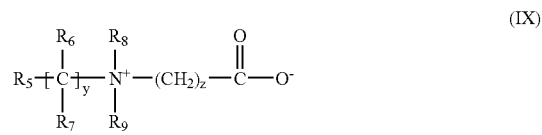

wherein $R_5$ is chosen from polymerizable unsaturated groups, such as acrylate, methacrylate, acrylamide and methacrylamide groups; y and z, which may be identical or different, are each an integer ranging from 1 to 3; $R_6$ and $R_7$, which may be identical or different, are each chosen from hydrogen, methyl, ethyl and propyl; $R_8$ and $R_9$, which may be identical or different, are each chosen from hydrogen and alkyl groups such that the sum of the carbon atoms in $R_8$ and $R_9$ does not exceed 10.

The polymers comprising such units may also comprise units derived from non-zwitterionic monomers, such as dimethyl and diethylaminoethyl acrylates and methacrylates, alkyl acrylates and methacrylates, acrylamides and methacrylamides, and vinyl acetate.

For example, non-limiting mention may be made of the copolymer of butyl methacrylate/dimethyl carboxymethylammonio ethyl methacrylate, such as the product sold under the name Diaformer Z301 by the company Sandoz.

(5) Polymers derived from chitosan comprising monomer units of the following formulae (X), (XI) and (XII) below:

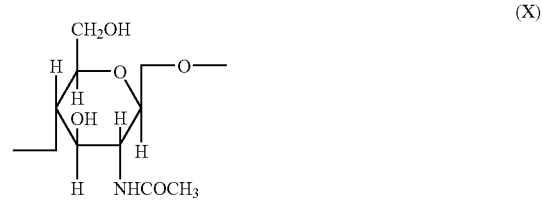

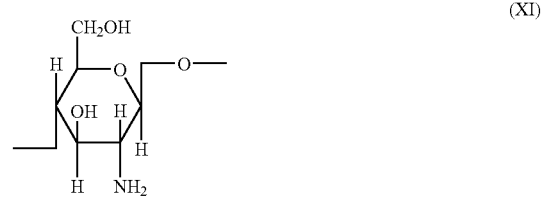

-continued

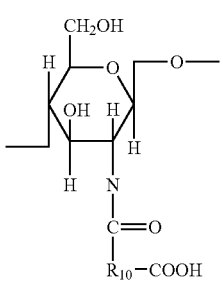
(XII)

wherein unit (X) is present in proportions ranging from 0% to 30%, unit (XI) is present in proportions ranging from 5% to 50%, and unit (XII) is present in proportions ranging from 30% to 90%, wherein, in the unit (XII), $R_{10}$ is a group of formula:

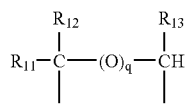

wherein if q=0, $R_{11}$, $R_{12}$ and $R_{13}$, which may be identical or different, are each chosen from hydrogen and methyl, hydroxyl, acetoxy and amino residues; monoalkylamine residues and dialkylamine residues which are optionally interrupted by at least one nitrogen and/or optionally substituted with at least one group chosen from amine, hydroxyl, carboxyl, alkylthio and sulphonic groups; and alkylthio residues wherein the alkyl group bears an amino residue, and at least one of the groups $R_{11}$, $R_{12}$ and $R_{13}$ is a hydrogen;

or if q=1, then $R_{11}$, $R_{12}$ and $R_{13}$, which may be identical or different, are each chosen from hydrogen, as well as the salts formed by these compounds with bases or acids.

(6) Polymers derived from the N-carboxyalkylation of chitosan, such as N-carboxymethylchitosan and N-carboxybutylchitosan sold under the name "Evalsan" by the company Jan Dekker.

(7) Polymers corresponding to the general formula (XIII) as described, for example, in French Patent No. 1,400,366:

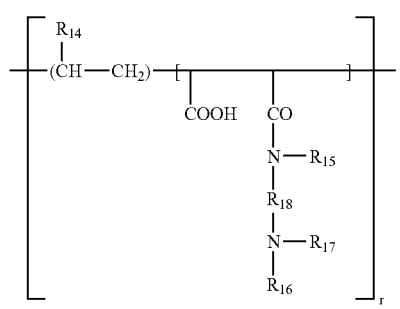
(XIII)

wherein $R_{14}$ is chosen from hydrogen and $CH_3O$, $CH_3CH_2O$ and phenyl groups; $R_{15}$ is chosen from hydrogen and lower alkyl groups, such as methyl and ethyl; $R_{16}$ is chosen from hydrogen and lower alkyl groups, such as methyl and ethyl; $R_{17}$ is chosen from lower alkyl groups, such as methyl and ethyl, and groups corresponding to the formula: $-R_{18}-N(R_{16})_2$, wherein, $R_{18}$ is chosen from $-CH_2-CH_2-$, $-CH_2-CH_2-CH_2-$ and $-CH_3$)-groups, and $R_{16}$ is chosen from hydrogen and lower alkyl groups, such as methyl and ethyl, and higher homologs of these groups and comprises up to 6 carbon atoms; and r is chosen such that the number-average molecular weight of said polymers ranges from 500 to 6,000,000, such as from 1,000 to 1,000,000.

(8) Amphoteric polymers of the type -D-X-D-X— chosen from:

a) polymers obtained by the action of chloroacetic acid or sodium chloroacetate on compounds comprising at least one unit of formula:

-D-X-D-X-D- (XIV)

wherein D is a group

and X is chosen from symbols E and E', wherein E and E', which may be identical or different, are chosen from divalent alkylene groups comprising at least one chain chosen from straight and branched chains comprising up to 7 carbon atoms in the main chain, wherein said divalent alkylene groups are optionally substituted with at least one hydroxyl group, wherein E and E' optionally comprise at least one atom chosen from oxygen, nitrogen and sulphur atoms, and 1 to 3 rings chosen from aromatic and heterocyclic rings. The oxygen, nitrogen and sulphur atoms are optionally present in the form of at least one group chosen from ether, thioether, sulphoxide, sulphone, sulphonium, alkylamine, alkenylamine, hydroxyl, benzylamine, amine oxide, quaternary ammonium, amide, imide, alcohol, ester and urethane groups;

b) polymers of formula:

-D-X-D-X- (XV)

wherein D is a group

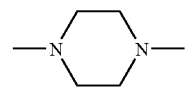

and X is chosen from symbols E and E' and wherein at least one X is chosen from E'; E having the meaning given above and E' being chosen from divalent alkylene groups comprising at least one chain chosen from straight and branched chains comprising up to 7 carbon atoms in the main chain, wherein said divalent alkylene groups are optionally substituted with at least one hydroxyl group. E' optionally comprises at least one nitrogen atom substituted with an alkyl chain, which is optionally interrupted by an oxygen atom, wherein said alkyl chain comprises at least one functional group chosen from carboxyl functional groups and hydroxyl functional groups, and wherein the alkyl chain is betainized by reaction with a reactant chosen from chloroacetic acid and sodium chloroacetate.

(9) ($C_1$-$C_5$)alkyl vinyl ether/maleic anhydride copolymers partially modified by semiamidation with an N,N-dialkylaminoalkylamine, such as N,N-dimethylamino-propylamine or by semiesterification with an N,N-dialkanolamine. These copolymers can further comprise other vinyl comonomers, such as vinylcaprolactam.

The amphoteric polymers that are, for example, used herein include those of family (1), such as copolymers of a dimethyldiallylammonium salt (for example, a halide) and of acrylic acid.

As disclosed herein, the at least one polymer chosen from cationic and amphoteric polymers may be present in an amount ranging from 0.001% to 20% by weight, for example, from 0.01% to 10% by weight, and further, for example, from 0.1% to 5% by weight, relative to the total weight of the composition.

According to one embodiment, the compositions disclosed herein further comprise at least one silicone or another agent that is beneficial to keratin materials, such as hair, for example, esters of $C_1$-$C_{30}$ carboxylic acids and of $C_1$-$C_{30}$ monohydroxylated or polyhydroxylated alcohols, plant, animal, mineral and synthetic oils, waxes, ceramides and pseudoceramides.

The additional silicones that may be used herein can, for example, include polyorganosiloxanes that are insoluble in the composition, and they may be in the form of oils, waxes, resins or gums and organomodified silicones.

These additional organopolysiloxanes are defined in greater detail in Walter Noll's "Chemistry and Technology of Silicones" (1968) Academic Press. They can be volatile or non-volatile.

When they are volatile, the additional silicones are, for example, chosen from those having a boiling point ranging from 60° C. to 260° C., and can also be chosen, for example, from:

(i) cyclic silicones comprising from 3 to 7 and, for example, from 4 to 5 silicon atoms. For example, octamethylcyclotetrasiloxanes sold, for instance, under the name "Volatile Silicone 207" by Union Carbide or "Silbione 70045 V 2" by Rhodia Chimie, decamethylcyclopentasiloxane sold under the name "Volatile Silicone 158" by Union Carbide, and "Silbione 70045 V 5" by Rhodia Chimie, and mixtures thereof can be used.

Non-limiting mention may also be made of cyclocopolymers of the dimethylsiloxanes/methylalkylsiloxane type, such as "Volatile Silicone FZ 3109" sold by the company Union Carbide, having the chemical structure:

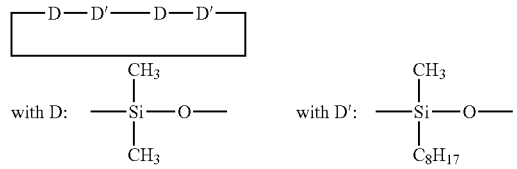

Additionally, non-limiting mention may also be made of mixtures of cyclic silicones with organosilicon compounds, such as mixtures of octamethylcyclotetrasiloxane and tetratrimethylsilylpentaerythritol (50/50) and mixtures of octamethylcyclotetrasiloxane and oxy-1,1'-bis(2,2,2',2',3,3'-hexatrimethylsilyloxy)neopentane;

(ii) linear volatile silicones comprising from 2 to 9 silicon atoms and having a viscosity of less than or equal to $5 \times 10^{-6}$ $m^2$/s at 25° C. For example, decamethyltetrasiloxanes sold, for instance, under the name "SH 200" by the company Toray Silicone can be used. Silicones belonging to this category are also described in the article published in Cosmetics and Toiletries, Vol. 91, Jan. 76, pp. 27-32, Todd & Byers "Volatile Silicone Fluids for Cosmetics".

These additional silicones are, for example, chosen from polyalkylsiloxanes, among which non-limiting mention may be made of polydimethylsiloxanes comprising trimethylsilyl end groups having a viscosity ranging from $5 \times 10^{-6}$ to 2.5 $m^2$/s at 25° C. and, for example, from $1 \times 10^{-5}$ to 1 $m^2$/s at 25° C. The viscosity of the silicones is measured, for example, at 25° C. according to ASTM standard 445 Appendix C.

Among these polyalkylsiloxanes, non-limiting mention may be made, of the following commercial products:

Silbione oils of the 47 and 70 047 series or the Mirasil oils sold by Rhodia Chimie, such as the oil 70 047 V 500 000;

oils of the Mirasil series sold by the company Rhodia Chimie;

oils of the 200 series from the company Dow Corning, such as DC200 with a viscosity of 60 000 cSt; and Viscasil oils from General Electric and oils of the SF series (SF 96, SF 18) from General Electric.

Non-limiting mention may also be made of polydimethylsiloxanes comprising dimethylsilanol end groups (Dimethiconol according to the CTFA name), such as the oils of the 48 series from the company Rhodia Chimie.

In this category of polyalkylsiloxanes, non-limiting mention may also be made of the products sold under the names "Abil Wax 9800 and 801" by the company Degussa, which are poly($C_1$-$C_{20}$)alkylsiloxanes.

The silicone gums that can be used as additives include, for example, polydiorganosiloxanes having high number-average molecular masses ranging from 200,000 to 1,000,000, used alone or as a mixture in a solvent. The solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, and mixtures thereof.

Non-limiting mention may be made, for example, of the following products:

polydimethylsiloxane, and polydimethylsiloxane/methylvinylsiloxane gums.

For example, products that can be used include mixtures, such as:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane; and mixtures of two PDMSs of different viscosities, and, for example, of a PDMS gum and a PDMS oil, such as the product SF 1236 from the company General Electric. The product SF 1236 is a mixture of an SE 30 gum defined above, having a viscosity of 20 $m^2$/s, and an SF 96 oil, with a viscosity of $5 \times 10^{-6}$ $m^2$/s. This product comprises, for example, 15% SE 30 gum and 85% SF 96 oil.

The organopolysiloxane resins that can be used as additives include crosslinked siloxane systems comprising the following units:

$R_2SiO_{2/2}$, $R_3SiO_{1/2}$, $RSiO_{3/2}$ and $SiO_{4/2}$ wherein R is chosen from hydrocarbon-based groups comprising from 1 to 16 carbon atoms and phenyl groups. Among these products, non-limiting mention may be made, for example, of the ones wherein R is chosen from $C_1$-$C_4$ lower alkyl groups, such as methyl and a phenyl group.

Among these resins, non-limiting mention may be made of the product sold under the name "Dow Corning 593" or those sold under the names "Silicone Fluid SS 4230 and SS 267" by the company General Electric, which are silicones of dimethyl/trimethyl siloxane structures.

Non-limiting mention may also be made of the trimethyl siloxysilicate type resins sold, for example, under the names X22-4914, X21-5034 and X21-5037 by the company Shin-Etsu.

The organomodified silicones that can be used herein include silicones as defined above and comprising in their structure at least one organofunctional group attached via a hydrocarbon-based group.

Among the organomodified silicones, non-limiting mention may be made of polyorganosiloxanes comprising:

at least one group chosen from polyethyleneoxy and polypropyleneoxy groups optionally comprising at least one alkyl group chosen from $C_6$-$C_{24}$ alkyl groups, such as the products known as dimethicone copolyol sold by the company Dow Corning under the name DC 1248 or the oils Silwet L 722, L 7500, L 77 and L 711 by the company Union Carbide, and the ($C_{12}$)alkylmethicone copolyol sold by the company Dow Corning under the name Q2 5200;

optionally substituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups include, for example, $C_1$-$C_4$ aminoalkyl groups;

thiol groups, such as the products sold under the names "GP 72 A" and "GP 71" from Genesee;

alkoxylated groups, such as the product sold under the name "Silicone Copolymer F-755" by SWS Silicones and Abil Wax 2428, 2434 and 2440 by the company Goldschmidt;

hydroxylated groups, such as the polyorganosiloxanes comprising a hydroxyalkyl functional group, described in French Patent Application No. 85/16334;

acyloxyalkyl groups, such as the polyorganosiloxanes described in U.S. Pat. No. 4,957,732;

anionic groups of carboxylic type, such as in the products described in Patent No. EP 186 507 from the company Chisso Corporation, or of alkylcarboxylic type, such as those present in the product X-22-3701E from the company Shin-Etsu; 2-hydroxyalkyl sulphonate; 2-hydroxyalkyl thiosulphate, such as the products sold by the company Goldschmidt under the names "Abil S201" and "Abil S255";

hydroxyacylamino groups, such as the polyorganosiloxanes described in Patent Application No. EP 342 834. Non-limiting mention may be made, for example, of the product Q2-8413 from the company Dow Corning.

As disclosed herein, it is also possible to use silicones comprising a polysiloxane portion and a portion comprising a nonsilicone organic chain, wherein one of the two portions constitutes the main chain of the polymer, the other is grafted onto the main chain. These polymers are described, for example, in Patent Application Nos. EP-A-412 704, EP-A-412 707, EP-A-640 105, WO 95/00578, EP-A-582 152 and WO 93/23009 and U.S. Pat. Nos. 4,693,935, 4,728,571 and 4,972,037. These polymers can, for example, be chosen from anionic and nonionic polymers.

Such polymers are, for example, copolymers that can be obtained by free-radical polymerization starting with a monomer mixture comprising:

a) 50% to 90% by weight of tert-butyl acrylate;

b) 0% to 40% by weight of acrylic acid;

c) 5% to 40% by weight of silicone macromer of formula:

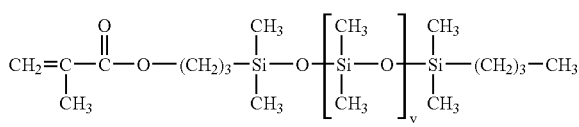

wherein v is a number ranging from 5 to 700; and the weight percentages are calculated relative to the total weight of the monomers.

Other examples of grafted silicone polymers are polydimethylsiloxanes (PDMS) onto which are grafted, via a connecting chain unit of thiopropylene type, mixed polymer units of poly(meth)acrylic acid type and of polyalkyl(meth)acrylate type and polydimethylsiloxanes (PDMS) onto which are grafted, via a connecting chain unit of thiopropylene type, polymer units of polyisobutyl(meth)acrylate type.

As disclosed herein, the silicones can also be used in unmodified form or in the form chosen from solutions, emulsions, nanoemulsions and microemulsions.

For example, non-limiting mention can be made of the following silicones:

non-volatile silicones chosen from the family of polyalkylsiloxanes comprising trimethylsilyl end groups, such as oils having a viscosity ranging from 0.2 to 2.5 $m^2/s$ at 25° C., such as the oils of the DC200 series from Dow Corning, such as oils with a viscosity of 60,000 cSt, of the Mirasil DM series and, for example, the oil Mirasil DM 500 000 sold by the company Rhodia Chimie, and the silicone oil AK 300 000 sold by the company Wacker, polyalkylsiloxanes comprising dimethylsilanol end groups, such as dimethiconol, and polyalkylarylsiloxanes, such as the oil Mirasil DPDM sold by the company Rhodia Chimie;

polysiloxanes comprising amine groups, such as amodimethicones and trimethylsilylamodimethicones.

As disclosed herein, the additional silicones or the other additional beneficial agents may be present in an amount ranging from 0.001% to 20% by weight, for example, from 0.01% to 10% by weight, and further, for example, from 0.1% to 5% by weight, relative to the total weight of the composition.

The compositions disclosed herein further comprise at least one surfactant which is generally present in an amount ranging from 0.01% to 50% by weight, for example, from 0.1% to 40% by weight, and further, for example, from 0.5% to 30% by weight, relative to the total weight of the composition.

The at least one surfactant may be chosen from anionic, amphoteric, nonionic and cationic surfactants, and mixtures thereof.

The at least one surfactant that can be used herein are chosen, for example, from the following surfactants:

(i) Anionic Surfactants:

Thus, as examples of the anionic surfactants, which can be used herein, alone or as mixtures, non-limiting mention may be made, for example, of salts (for example, alkaline salts, such as sodium salts, ammonium salts, amine salts, amino alcohol salts and magnesium salts), of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, alkyl and acyl groups of all of these various compounds comprising, for example, from 8 to 24 carbon atoms, and aryl groups chosen, for example, from phenyl and benzyl groups. Among the anionic surfactants which can also be used, non-limiting mention may also be made of fatty acid salts, such as the salts of oleic, ricinoleic, palmitic and stearic acids, coconut oil acid and hydrogenated coconut oil acid; acyl lactylates, wherein the acyl group comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof.

For example, the anionic surfactants that can be used herein include alkyl sulphate salts and alkyl ether sulphate salts and mixtures thereof.

(ii) Nonionic Surfactants:

The nonionic surfactants are compounds that are well known per se (see, for example, "Handbook of Surfactants" by M. R. Porter, published by Blackie & Son (Glasgow and London), 1991, pp. 116-178). Thus, they can be chosen, for example, from (nonlimiting list) polyethoxylated, polypropoxylated and polyglycerolated fatty acids, alkylphenols, α-diols and alcohols comprising a fatty chain comprising, for example, from 8 to 18 carbon atoms, it being possible for the number of ethylene oxide or propylene oxide groups to range, for example, from 2 to 50 and for the number of glycerol groups to range, for example, from 2 to 30. Non-limiting mention may also be made of copolymers of ethylene oxide and of propylene oxide, condensates of ethylene oxide and of propylene oxide with fatty alcohols; polyethoxylated fatty amides comprising, for example, from 2 to 30 mol of ethylene oxide, polyglycerolated fatty amides comprising, for example, on average, from 1 to 5 glycerol groups, and further, for example, from 1.5 to 4 glycerol groups; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides, such as ($C_{10}$-$C_{14}$)alkylamine oxides and N-acylaminopropylmorpholine oxides. For example, the nonionic surfactants that can be used herein are chosen from alkylpolyglycosides.

(iii) Amphoteric Surfactants:

The amphoteric surfactants, can, for example, be chosen from (nonlimiting list), aliphatic secondary and tertiary amine derivatives, wherein the aliphatic group is chosen from linear and branched chains comprising from 8 to 22 carbon atoms and comprising at least one water-soluble anionic group chosen, for example, from carboxylates, sulphonates, sulphates, phosphates and phosphonates. The amphoteric surfactants may also be chosen from ($C_8$-$C_{20}$)alkylbetaines, sulphobetaines, ($C_8$-$C_{20}$)alkylamido($C_1$-$C_6$)alkylbetaines and ($C_8$-$C_{20}$)alkylamido($C_1$-$C_6$)alkylsulphobetaines.

Among the ($C_8$-$C_{20}$)alkylamido($C_1$-$C_6$)alkylbetaines, non-limiting mention may be made of cocoamidopropylbetaine sold, for example, by Degussa under the name Tegobetaine F50.

For example, the amine derivatives may also be chosen from products sold under the name Miranol, as described in U.S. Pat. Nos. 2,528,378 and 2,781,354 and having the structures (2) and (3) may be used:

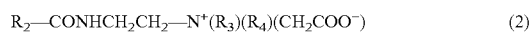

$$R_2-CONHCH_2CH_2-N^+(R_3)(R_4)(CH_2COO^-) \quad (2)$$

wherein: $R_2$ is chosen from alkyl groups derived from an acid $R_2$—COOH present in hydrolysed coconut oil, and heptyl, nonyl and undecyl groups, $R_3$ is a β-hydroxyethyl group and $R_4$ is a carboxymethyl group;

and

$$R_5-CONHCH_2CH_2-N(B)(C) \quad (3)$$

wherein:

B is chosen from —$CH_2CH_2OX'$ groups, C is chosen from —$(CH_2)_z$—$Y'$ groups, wherein z=1 or 2, X' is chosen from the —$CH_2CH_2$—COOH group and hydrogen, Y' is chosen from —COOH and —$CH_2$—CHOH—$SO_3H$ groups, $R_5$ is chosen from alkyl groups of an acid $R_5$—COOH present in coconut oil or in hydrolysed linseed oil, alkyl groups, such as $C_7$, $C_9$, $C_{11}$ and $C_{13}$ alkyl groups, a $C_{17}$ alkyl group and its iso form, and an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylamphodipropionate, lauroamphodipropionic acid, and cocoamphodipropionic acid.

For example, the cocoamphodiacetate sold under the trade name Miranol C2M concentrate by the company Rhodia Chimie may be used.

(iv) Cationic Surfactants:

The cationic surfactants may be chosen, for example, from:

A) the quaternary ammonium salts of general formula (XVI) below:

(XVI)

wherein $X^-$ is an anion chosen from halides (such as chloride, bromide and iodide) and ($C_2$-$C_6$)alkyl sulphates, such as methyl sulphate, phosphates, alkyl and alkylaryl sulphonates, and anions derived from organic acids, such as acetate and lactate, and a) $R_1$, $R_2$, and $R_3$, which may be identical or different, can each be chosen from linear and branched aliphatic groups comprising from 1 to 4 carbon atoms, and aromatic groups, such as aryl and alkylaryl groups. The aliphatic groups can comprise at least one hetero atom chosen, for example, from oxygen, nitrogen, sulphur and halogens. The aliphatic groups are chosen, for example, from alkyl, alkoxy and alkylamide groups, $R_4$ is chosen from linear and branched alkyl groups comprising from 16 to 30 carbon atoms; or b) $R_1$ and $R_2$, which may be identical or different, can each be chosen from linear and branched aliphatic groups comprising from 1 to 4 carbon atoms, and aromatic groups, such as aryl and alkylaryl groups. The aliphatic groups can comprise at least one hetero atom chosen, for example, from oxygen, nitrogen, sulphur and halogens. The aliphatic groups are chosen, for example, from alkyl, alkoxy, alkylamide and hydroxyalkyl groups comprising, for example, from 1 to 4 carbon atoms;

$R_3$ and $R_4$, which may be identical or different, are each chosen from linear and branched alkyl groups comprising from 12 to 30 carbon atoms, wherein the alkyl group comprises at least one functional group chosen from ester and amide functional groups.

$R_3$ and $R_4$, which may be identical or different, can, for example, be chosen from $(C_{12}-C_{22})$alkylamido$(C_2-C_6)$alkyl and $(C_{12}-C_{22})$alkylacetate groups.

For example, the cationic surfactants can be chosen from behenyltrimethylammonium salts, such as chloride.

For example, the cationic surfactant is chosen from stearamidopropyldimethyl(myristyl acetate)ammonium salts, such as chloride.

B)—quaternary ammonium salts of imidazolinium, such as those of formula (XVII) below:

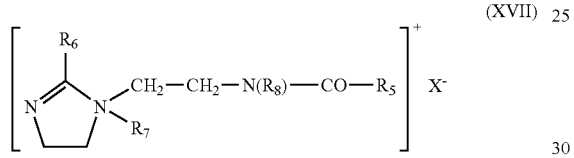

wherein $R_5$ is chosen from alkenyl and alkyl groups comprising from 8 to 30 carbon atoms, for example, fatty acid derivatives of tallow, $R_6$ is chosen from hydrogen, $C_1-C_4$ alkyl groups and alkenyl and alkyl groups comprising from 8 to 30 carbon atoms, $R_7$ is chosen from $C_1-C_4$ alkyl groups, $R_8$ is chosen from hydrogen and $C_1-C_4$ alkyl groups, and $X^-$ is an anion chosen from halides, phosphates, acetates, lactates, alkyl sulphates, alkyl sulphonates and alkylaryl sulphonates. $R_5$ and $R_6$, which may be identical or different, can, for example, be chosen from mixtures of alkenyl and alkyl groups comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat" W75, W90, W75PG and W75HPG by the company Witco, C)—diquaternary ammonium salts of formula (XVIII):

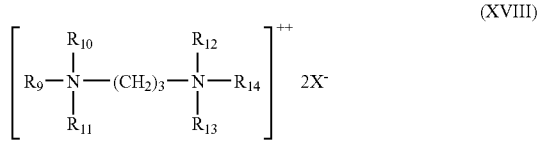

wherein $R_9$ is chosen from aliphatic groups comprising from 16 to 30 carbon atoms, $R_{10}$, $R_{11}$, $R_{12}$, $R_{13}$ and $R_{14}$, which may be identical or different, are each chosen from hydrogen and alkyl groups comprising from 1 to 4 carbon atoms, and $X^-$ is an anion chosen from halides, acetates, phosphates, nitrates and methyl sulphates. Such diquaternary ammonium salts can, for example, comprise propanetallowdiammmonium dichloride;

D)—quaternary ammonium salts comprising at least one ester functional group, of formula (XIX) below:

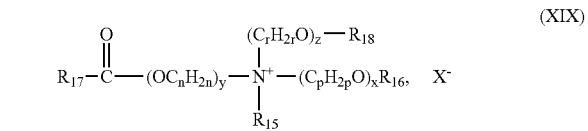

wherein:

$R_{15}$ is chosen from $C_1-C_6$ alkyl groups and $C_1-C_6$ hydroxyalkyl and dihydroxyalkyl groups;

$R_{16}$ is chosen from:

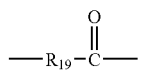

groups,
linear and branched, saturated and unsaturated $C_1-C_{22}$ hydrocarbon-based groups $R_{20}$, and
hydrogen, $R_{18}$ is chosen from:

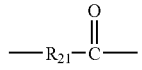

groups,
linear and branched, saturated and unsaturated $C_1-C_6$ hydrocarbon-based groups $R_{22}$, and
hydrogen, $R_{17}$, $R_{19}$ and $R_{21}$, which may be identical or different, are each chosen from linear and branched, saturated and unsaturated $C_7-C_{21}$ hydrocarbon-based groups;

n, p and r, which may be identical or different, are each an integer ranging from 2 to 6;

y is an integer ranging from 1 to 10;

x and z, which may be identical or different, are each an integer ranging from 0 to 10;

$X^-$ is an anion chosen from simple, complex, organic, and inorganic anions;

with the proviso that the sum x+y+z ranges from 1 to 15, that when x is 0, then $R_{16}$ is $R_{20}$ and that when z is 0, then $R_{18}$ is $R_{22}$.

For example, the ammonium salts of formula (XIX) may be used, wherein:

$R_{15}$ is chosen from methyl and ethyl groups, x and y are equal to 1;

z is equal to 0 or 1;

n, p and r are equal to 2;

$R_{16}$ is chosen from:

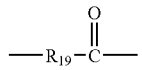

groups,
methyl, ethyl and $C_{14}-C_{22}$ hydrocarbon-based groups, and hydrogen;

$R_{17}$, $R_{19}$ and $R_{21}$, which may be identical or different, are each chosen from linear and branched, saturated and unsaturated $C_7$-$C_2$, hydrocarbon-based groups;

$R_{18}$ is chosen from:

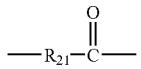

groups, and hydrogen.

Such compounds are sold, for example, under the names Dehyquart by the company Cognis, Stepanquat by the company Stepan, Noxamium by the company Ceca, and Rewoquat WE 18 by the company Rewo-Witco.

Among the quaternary ammonium salts, non-limiting mention may be made of behenyltrimethylammonium chloride and stearamidopropyldimethyl(myristyl acetate)ammonium chloride, sold under the name "Ceraphyl 70" by the company Van Dyk, and Quaternium-27 or Quaternium-83 sold by the company Witco.

In the compositions disclosed herein, it is possible to use mixtures of surfactants, such as mixtures of anionic surfactants, mixtures of anionic surfactants and of amphoteric, cationic or nonionic surfactants, and mixtures of cationic surfactants with nonionic or amphoteric surfactants. For example, the mixture comprising at least one anionic surfactant and at least one amphoteric surfactant may be used.

The composition disclosed herein may further comprise at least one additive chosen from thickeners, fragrances, nacres, preserving agents, silicone and non-silicone sunscreens, anionic and nonionic non-silicone polymers, non-cationic proteins, non-cationic protein hydrolysates, 18-methyleicosanoic acid, hydroxy acids, vitamins, provitamins, such as panthenol, and any other additive conventionally used in cosmetics that does not affect the properties of the compositions disclosed herein.

The compositions disclosed herein may, for example, comprise up to 5% of nacres or opacifiers that are well known in the prior art, for instance, sodium and magnesium palmitates, sodium and magnesium stearates and hydroxystearates, fatty-chain acyl derivatives, such as ethylene glycol and polyethylene glycol monostearate and distearate, fatty-chain ethers, for instance, distearyl ether and 1-(hexadecyloxy)-2-octadecanol, and fatty alcohols, such as stearyl alcohol, cetyl alcohol and behenyl alcohol, and mixtures thereof.

The at least one additive is optionally present in the composition disclosed herein in an amount that may range from 0.001% to 20% by weight, relative to the total weight of the composition. The precise amount of each additive is readily determined by a person of ordinary skill in the art according to its nature and its function.

The physiologically and, for example, cosmetically acceptable medium may comprise solely water or a mixture of water and of at least one cosmetically acceptable solvent, such as $C_1$-$C_4$ lower alcohols, for instance ethanol, isopropanol, tert-butanol and n-butanol; alkylene glycols, such as propylene glycol, and glycol ethers.

For example, the composition comprises from 50% to 95% by weight of water, and, for instance, from 60% to 90% by weight of water, relative to the total weight of the composition.

The compositions disclosed herein have a final pH generally ranging from 3 to 10. This pH can range, for example, from 4 to 8. The pH may be adjusted to the desired value conventionally by adding a base (organic or mineral base) to the composition, for example, aqueous ammonia or a primary, secondary or tertiary (poly)amine, for instance, monoethanolamine, diethanolamine, triethanolamine, isopropanolamine or 1,3-propanediamine, or by adding a mineral or organic acid, for example, a carboxylic acid, such as citric acid.

The compositions disclosed herein may be used, for example, for washing or treating keratin materials such as hair, skin, eyelashes, eyebrows, nails, lips and scalp. In one embodiment, the keratin material is hair.

The compositions disclosed herein may be detergent compositions, such as shampoos, shower gels and bubble bath compositions. In one embodiment, the compositions comprise at least one washing base, which is generally aqueous.

The washing base comprises at least one surfactant, which may be chosen, alone or as mixtures, from anionic, amphoteric, nonionic and cationic surfactants as defined above. The washing base comprises at least one detergent surfactant.

At least one anionic surfactant or mixtures of at least one anionic surfactant and of at least one amphoteric surfactant or of at least one nonionic surfactant can, for example, be used in the compositions disclosed herein.

For example, the mixture comprising at least one anionic surfactant and at least one amphoteric surfactant may be used.

The anionic surfactant used herein can be chosen, for example, from sodium, triethanolamine and ammonium ($C_{12}$-$C_{14}$)alkyl sulphates, sodium, triethanolamine and ammonium ($C_{12}$-$C_{14}$)alkyl ether sulphates oxyethylenated with 2.2 mol of ethylene oxide, sodium cocoyl isethionate and sodium ($C_{14}$-$C_{16}$)-$\alpha$-olefin sulphonate and mixtures thereof with:

either at least one amphoteric surfactant, such as the amine derivatives known as disodium cocoamphodipropionate and sodium cocoamphopropionate sold, for example, by the company Rhodia Chimie under the trade name "Miranol C2M Conc." as an aqueous solution comprising 38% active material, or under the name Miranol C32;

or at least one amphoteric surfactant of zwitterionic type, such as alkylbetaines and alkylamidobetaines and, for example, the cocobetaine sold under the name "Dehyton AB 30" as an aqueous solution comprising 32% active material by the company Cognis, and the cocoamidopropylbetaine sold, for example, by Degussa under the name Tegobetaine F50.

In one embodiment, the quantity and quality of the washing base used are those that are sufficient to give the final composition a satisfactory foaming and/or detergent power.

These detergent compositions are, for example, foaming compositions and the foaming power of the compositions disclosed herein is characterized by a foam height, which is generally greater than 75 mm and, for example, greater than 100 mm, measured according to the modified Ross-Miles method (NF T 73-404/ISO 696).

The modifications to the method are as follows:

The measurement is performed at a temperature of 22° C. with osmosed water. The concentration of the solution is 2 g/l. The drop height is 1 m. The amount of composition which is dropped is 200 ml The 200 ml of composition fall into a measuring cylinder 50 mm in diameter and comprising 50 ml of the test composition. The measurement is carried out 5 minutes after stopping the flow of the composition.

Thus, according to the present disclosure, the detergent surfactants may be present in an amount ranging from 3% to 50% by weight, for example, from 6% to 35% by weight, and further, for example, from 8% to 25% by weight, relative to the total weight of the composition.

Further disclosed herein is a process for treating keratin materials, such as skin and hair, comprising applying to the keratin materials a cosmetic composition as defined above and then optionally rinsing the keratin materials with water.

Thus, the process, as disclosed herein, can allow hold of the hairstyle, and the treatment, care or washing of or the removal of makeup from the skin, the hair or any other keratin material.

The compositions disclosed herein may also be in the form chosen from rinse-out and leave-in conditioners, permanent-waving, hair-relaxing, dyeing and bleaching compositions, or in the form chosen from rinse-out compositions, to be applied before or after dyeing, bleaching, permanent-waving and relaxing the hair or between the two steps of permanent-waving and hair-relaxing operations.

When the composition is in the form of a conditioner optionally to be rinsed out, it can, for example, comprise at least one cationic surfactant, wherein the at least one cationic surfactant can be present in an amount ranging from 0.1% to 10% by weight, and, for example, from 0.5% to 5% by weight, relative to the total weight of the composition.

The compositions disclosed herein may also be in the form of washing compositions for the skin, and, for example, in the form chosen from bath and shower solutions and gels, and makeup-removing products.

The compositions disclosed herein may also be in the form of aqueous or aqueous-alcoholic lotions for skincare and/or haircare.

The cosmetic compositions disclosed herein may be in the form chosen from gels, milks, creams, emulsions, thickened lotions and mousses and may be used for skin, nails, eyelashes, lips and, for example, hair.

The compositions may be packaged in various forms, such as in vaporizers, pump-dispenser bottles and aerosol containers in order to be able to apply the composition in a vaporized form or in the form of a mousse. Such packaging forms are indicated, for example, when it is desired to obtain a spray, a lacquer or a mousse for treating keratin materials, such as hair. As disclosed herein, the percentages are expressed on a weight basis.

The present disclosure will now be illustrated more fully with the aid of the non-limiting examples that follow.

In the examples, AM means Active Material.

EXAMPLE 1

The shampoo composition, as disclosed herein comprising the composition below, was prepared:

| Composition | Example 1 |
| --- | --- |
| Sodium lauryl ether sulphate comprising 2.2 mol of ethylene oxide | 12.5 g AM |
| Sodium cocoamidoethyl(N-hydroxyethyl-N-carboxymethyl)glycinate (Miranol C2M from Rhodia) | 2.5 g AM |
| Methacrylic acid/ethyl acrylate crosslinked copolymer as an aqueous emulsion comprising 30% A.M., sold under the name Carbopol Aqua SF1 by the company Noveon | 3 g AM |
| Aluminium oxide (aluminium oxide C from Degussa-Huls) | 0.5 g |
| Hydroxyethylcellulose crosslinked with epichlorohydrin, quaternized with trimethylamine (JR400 from Amerchol) | 0.5 g |
| Preserving agents, fragrance | q.s. |
| pH agent q.s. | pH 6.5 |
| Demineralized water q.s. | 100 g |

The composition was stable. The wet hair treated with the shampoo composition was not laden and was easy to shape.

EXAMPLE 2

The shampoo, as disclosed herein, comprising the composition below, was prepared:

| | |
| --- | --- |
| Sodium lauryl sulphate | 12.5 g AM |
| Cocoamidopropylbetaine | 2.5 g AM |
| Polyethyleneimine (Lupasol from BASF) | 0.025 g |
| Calcium carbonate | 5 g |
| Methacrylic acid/ethyl acrylate crosslinked copolymer as an aqueous emulsion comprising 30% AM, sold under the name Carbopol Aqua SF1 by the company Noveon | 3 g AM |
| Preserving agents q.s. | |
| Demineralized water q.s. | 100 g |

EXAMPLES 3 and 4

Two shampoos, as disclosed herein, comprising the compositions below, were prepared:

| Composition | Example 3 | Example 4 |
| --- | --- | --- |
| Sodium lauryl ether sulphate comprising 2.2 mol of ethylene oxide | 11.2 g AM | 15.5 g AM |
| Cocoylbetaine | — | 2.4 g AM |
| Sodium cocoamidoethyl(N-hydroxyethyl-N-carboxymethyl)glycinate (Miranol C2M from Rhodia) | 3.8 g AM | — |
| Methacrylic acid/ethyl acrylate copolymer as an aqueous emulsion comprising 30% active material, sold by the company Noveon | 2.7 g | 2.7 g |
| 1-(Hexadecyloxy)-2-octadecanol/cetyl alcohol mixture | — | 2.5 g |
| Selenium disulphide | — | 1 g |
| Kaolin | 3 g | — |
| Polydimethylsiloxane of viscosity 500 000 cSt (Mirasil DM 500 000 from Rhodia) | — | 1.5 g |
| Hydroxyethylcellulose crosslinked with epichlorohydrin, quaternized with trimethylamine (JR 400 from Amerchol) | — | 0.4 g |
| Guar gum modified with 2,3-epoxy-propyltrimethylammonium chloride (Jaguar C13 S from Rhodia) | 0.1 g | — |
| Sodium hypochlorite as an aqueous 14% solution | — | 0.05 g AM |
| Salicylic acid | — | 1 g |
| Sodium chloride | 3 g | — |
| Citric acid | 0.6 g | — |
| Preserving agents, fragrance | q.s. | q.s. |
| pH agent q.s. | pH 5 | pH 4 |
| Demineralized water q.s. | 100 g | 100 g |

The compositions were stable, the wet hair treated with the shampoos was not laden and was easy to shape.

What is claimed is:

1. A cosmetic composition comprising, in a cosmetically acceptable medium,
    crosslinked copolymer comprising at least one methacrylic acid unit and at least one $C_1$-$C_4$ alkyl acrylate unit,
    cationic polymer chosen from polyethyleneimine and guar hydroxypropyl trimonium chloride, and
    water-insoluble solid mineral particle chosen from clays and particles comprising about 100% by weight of substantially pure of calcium carbonate, wherein the crosslinked copolymer is present in an amount ranging from 0.1% to 5% by weight, relative to the total weight of the composition, and the cationic polymer is present in an amount ranging from 0.01 % to 10% by weight, relative to the total weight of the composition, and the water insoluble solid mineral particle is present in an amount ranging from 0.01 % to 10% by weight, relative to the total weight of the composition.

2. The composition according to claim 1, wherein the cosmetic at least one methacrylic acid unit is present in an amount ranging from 20% to 80% by weight, relative to the total weight of the copolymer.

3. The composition according to claim 2, wherein the cosmetic at least one methacrylic acid unit is present in an amount ranging from 35% to 60% by weight, relative to the total weight of the copolymer.

4. The composition according to claim 1, wherein the cosmetic at least one alkyl acrylate unit is present in an amount ranging from 15% to 80% by weight, relative to the total weight of the copolymer.

5. The composition according to claim 4, wherein the cosmetic at least one alkyl acrylate unit is present in an amount ranging from 40% to 65% by weight, relative to the total weight of the copolymer.

6. The composition according to claim 1, wherein the cosmetic at least one alkyl acrylate unit is chosen from methyl acrylate, ethyl acrylate and butyl acrylate.

7. The composition according to claim 6, wherein the cosmetic at least one alkyl acrylate is ethyl acrylate.

8. The composition according to claim 1, wherein the cosmetic cationic polymer is polyethyleneimine.

9. The composition according to claim 1, wherein the cosmetic composition further comprises at least one silicone.

10. The composition according to claim 9, wherein the cosmetic at least one silicone is chosen from polyalkylsiloxanes comprising trimethylsilyl end groups, polyalkylsiloxanes comprising dimethylsilanol end groups, mixtures of two PDMSs comprising at least one gum and at least one oil with different viscosities, mixtures of organosiloxanes and of cyclic silicones, and organopolysiloxane resins.

11. The composition according to claim 1, wherein the cosmetic composition further comprises at least one agent that is beneficial to a keratin material, chosen from esters of $C_1$-$C_{30}$ carboxylic acids and of alcohols chosen from $C_1$-$C_{30}$ monohydroxylated and polyhydroxylated alcohols, plant, animal, mineral and synthetic oils, waxes, ceramides and pseudoceramides.

12. The composition according to claim 9, wherein the cosmetic at least one silicone is present in an amount ranging from 0.001% to 20% by weight, relative to the total weight of the composition.

13. The composition according to claim 11, wherein the cosmetic at least one agent that is beneficial to a keratin material is present in an amount ranging from 0.001% to 20% by weight, relative to the total weight of the composition.

14. The composition according to claim 1, wherein the cosmetic composition further comprises at least one surfactant chosen from anionic, nonionic, amphoteric and cationic surfactants, and mixtures thereof.

15. The composition according to claim 1, wherein the cosmetic composition is in a form chosen from shampoos, conditioners, compositions for permanent-waving, relaxing, dyeing and bleaching hair, rinse-out compositions to be applied between the two steps of a permanent-waving or hair-relaxing operation, and washing compositions for a body.

* * * * *

UNITED STATES PATENT AND TRADEMARK OFFICE
CERTIFICATE OF CORRECTION

PATENT NO. : 7,708,981 B2  Page 1 of 2
APPLICATION NO. : 10/796082
DATED : May 4, 2010
INVENTOR(S) : Miereille Maubru et al.

It is certified that error appears in the above-identified patent and that said Letters Patent is hereby corrected as shown below:

Claim 2, col. 29, line 9, "The composition" should read -- The cosmetic composition --.

Claim 2, col. 29, lines 9-10, after "wherein" delete "the cosmetic".

Claim 3, col. 29, line 13, "The composition" should read -- The cosmetic composition --.

Claim 3, col. 29, lines 13-14, after "wherein" delete "the cosmetic".

Claim 4, col. 29, line 17, "The composition" should read -- The cosmetic composition --.

Claim 4, col. 29, lines 17-18, after "wherein" delete "the cosmetic".

Claim 5, col. 29, line 22, "The composition" should read -- The cosmetic composition --.

Claim 5, col. 29, lines 22-23, after "wherein" delete "the cosmetic".

Claim 6, col. 29, line 26, "The composition" should read -- The cosmetic composition --.

Claim 6, col. 29, lines 26-27, after "wherein" delete "the cosmetic".

Claim 7, col. 29, line 29, "The composition" should read -- The cosmetic composition --.

Claim 7, col. 29, lines 29-30, after "wherein" delete "the cosmetic".

Claim 8, col. 29, line 31, "The composition" should read -- The cosmetic composition --.

Signed and Sealed this

Thirteenth Day of July, 2010

David J. Kappos
*Director of the United States Patent and Trademark Office*

Claim 8, col. 29, lines 31-32, after "wherein" delete "the cosmetic".

Claim 9, col. 29, line 33, "The composition" should read -- The cosmetic composition --.

Claim 9, col. 29, lines 33-34, after "wherein" delete "the cosmetic".

Claim 10, col. 30, line 1, "The composition" should read -- The cosmetic composition --.

Claim 10, col. 30, lines 1-2, after "wherein" delete "the cosmetic".

Claim 11, col. 30, line 8, "The composition" should read -- The cosmetic composition --.

Claim 11, col. 30, lines 8-9, after "wherein" delete "the cosmetic".

Claim 12, col. 30, line 15, "The composition" should read -- The cosmetic composition --.

Claim 12, col. 30, lines 15-16, after "wherein" delete "the cosmetic".

Claim 13, col. 30, line 19, "The composition" should read -- The cosmetic composition --.

Claim 13, col. 30, lines 19-20, after "wherein" delete "the cosmetic".

Claim 14, col. 30, line 23, "The composition" should read -- The cosmetic composition --.

Claim 14, col. 30, lines 23-24, after "wherein" delete "the cosmetic".

Claim 15, col. 30, line 27, "The composition" should read -- The cosmetic composition --.

Claim 15, col. 30, lines 27-28, after "wherein" delete "the cosmetic".